(12) United States Patent
Levon et al.

(10) Patent No.: US 9,243,275 B1
(45) Date of Patent: Jan. 26, 2016

(54) BIOSENSOR AND METHOD OF MAKING SAME

(75) Inventors: Kalle Levon, Brooklyn, NY (US); Bin Yu, West Hardford, CT (US); Yanxiu Zhou, West Hartford, CT (US)

(73) Assignee: Polytechnic Institute of New York University, Brooklyn, NY (US)

(*) Notice: Subject to any disclaimer, the term of this patent is extended or adjusted under 35 U.S.C. 154(b) by 1769 days.

(21) Appl. No.: 10/888,342

(22) Filed: Jul. 9, 2004

Related U.S. Application Data

(60) Provisional application No. 60/486,088, filed on Jul. 10, 2003.

(51) Int. Cl.
| | |
|---|---|
| C12Q 1/00 | (2006.01) |
| C07K 9/00 | (2006.01) |
| C07K 14/32 | (2006.01) |
| C07K 17/00 | (2006.01) |
| G01N 33/53 | (2006.01) |

(52) U.S. Cl.
CPC .... *C12Q 1/00* (2013.01); *C07K 9/00* (2013.01); *C07K 14/32* (2013.01); *C07K 17/00* (2013.01); *G01N 33/53* (2013.01)

(58) Field of Classification Search
None
See application file for complete search history.

(56) References Cited

U.S. PATENT DOCUMENTS

| | | | | |
|---|---|---|---|---|
| 5,413,690 A | * | 5/1995 | Kost et al. | 205/777.5 |
| 5,622,872 A | * | 4/1997 | Ribi | 436/518 |
| 6,329,209 B1 | * | 12/2001 | Wagner et al. | 436/518 |
| 2001/0026915 A1 | * | 10/2001 | Charych et al. | 435/5 |
| 2003/0138845 A1 | * | 7/2003 | Li et al. | 435/7.1 |
| 2005/0237480 A1 | * | 10/2005 | Allbritton et al. | 351/160 R |

OTHER PUBLICATIONS

Paddle (Biosensors & Bioelectronics. 1996. vol. 11(11):1079-1113).*
Feignier et al, (FEMS Microbio. Letters. 1995. vol. 127:11-15).*
Harada et al., (Langmuir. 2003. vol. 19:5104-5114).*
Noda et al., (FEMS Microbiolo. Letters. 2001. vol. 205:340-354).*
Ji et al. 2003 (Polymeric Recognition of Bacterial Spores; Extended Abstract in Proceedings from the American Chemical Society; Mar. 23-27, 2003) vol. 44; p. 483.*
Hartmann et al. 1995 (One-step immobilization of immunoglobulin G and potential of the method for application in immunosensors; Sensors and Actuators B 28: 143-149).*

(Continued)

*Primary Examiner* — Gary Nickol
*Assistant Examiner* — Mary Lyons
(74) *Attorney, Agent, or Firm* — Frommer Lawrence & Haug LLP; Stephen J. Lieb

(57) ABSTRACT

Sensors suitable for the sensing/detection of biological or chemical agents may be fabricated by immobilizing biological and/or chemical recognition components (selectors or probes) on a substrate by the polymerization of a suitable monomer in the presence of the selectors or probes, for example, by Polysiloxane Monolayer Immobilization (PMI). PMI may involve the polymerization of polysiloxane onto a substrate, onto which selector molecules are adsorbed or otherwise immobilized. The resulting immobilized selector molecule may then be used to interact with specific molecules (targets) within a mixture of molecules, thereby enabling those specific molecules to be detected and/or quantified.

17 Claims, 12 Drawing Sheets

(56) References Cited

OTHER PUBLICATIONS

Yan et al. 2000 (Preparation and characterization of self-assembled monolayers on Indium Tin Oxide; Langmuir, 16:6208-6215).*

Slentz et al. 2002 (Capillary electrochromatography of peptides on microfabricated poly(dimethylsiloxane) chips modified by cerium(IV)-catalyzed polymerization.*

PCT/ISA/220, "Notification of Transmittal of the International Search Report and the Written Opinion of the International Searching Authority, or the Declaration" for PCT/US04/21883, mailed May 1, 2008 (1 pg.).

PCT/ISA/210, "International Search Report" for PCT/US04/21883, mailed May 1, 2008 (3 pgs.).

PCT/ISA/237, "Written Opinion of the International Searching Authority" for PCT/US04/21883, mailed May 1, 2008 (5 pgs.).

* cited by examiner

*B. subtilis*

*B. thur. kurstaki*

BIOSENSOR AND METHOD OF MAKING SAME

§0 CROSS REFERENCE TO RELATED APPLICATIONS

This application claims the benefit of U.S. Provisional Patent Application Ser. No. 60/486,088 (incorporated herein by reference), titled "BACTERIAL BIOSENSOR," filed on Jul. 10, 2003 and listing Kalle Levon, Bin Yu, and Yanxiu Zhou as inventors.

§1. BACKGROUND

§1.1. Field of the Invention

This invention relates generally to the field of sensors and in particular to biosensors specific to biological/chemical agents and bacterium such as *Bacillus anthracis*.

§1.2. Background of the Invention

The potential use of anthrax, and in particular the spores of *Bacillus anthracis* (BA) as a weapon of biological terrorism has rekindled interest in devices and methods for the rapid detection and identification of biological or chemical agents. Such interest has become particularly acute since the September 11 attacks and the anthrax-by-mail terrorism.

Devices and methods for detecting biological or chemical agents should be rapid, specific, easy to use and transport, and very sensitive since a single pathogenic organism may be an infectious dose in some cases. Consequently, it is important to assess and begin treatment early for individuals exposed to such organisms. Additionally, it is equally important to know whether a person exhibiting general symptoms is suffering from, for example, anthrax exposure, or a less serious ailment for which totally different (or perhaps antagonistic) treatments are indicated.

§1.3. RELATED ART

Significant technological progress has been made in the detection and analysis of biological and chemical agents over the past decade. (See, for example: Ivnitski, D., Abdel-Hamid, I., Atanasov, P., Wilkins, E. *Biosensors Bioelectron.*, 1999, 14, 599-624 and references therein (875); and Iqbal, S. S., Mayo, M. W., Bruno, J. G., Bronk, B. V., Batt, C. A., Chambers, J. P. *Biosensor Bioelectron.*, 2000, 15, 549-578 and references therein (881).)

The outer face of macromolecular biological assemblies like viruses or bacteria includes a proteinaceous capsid, a membrane composed of glycoproteins and lipids, or a cell wall. Accordingly, they carry charged or chargeable groups on their outer surface creating an electric double layer upon contact with the aqueous phase. (See, for example: Kenndler, E., Blass, D. *Trends in Anal. Chem.*, 2001, 20(10), 543-551; and Lanza, R. P., Langer, R., Chick, W. L. (Eds). When a biological recognition component for bacterial spores, such as a peptides, nucleic acids (See, for example, Park, S.-J, Taton, T. A., Mirkin, C. A. *Science*, 2002, 295, 1a503-1506.), apatamers (See, for example, Bruno, J. G., Kiel, J. L. *Biosensor Bioelectron.*, 1999, 14, 457-464.), or antibodies (See, for example, Zhou, B., Wirsching, P., Janda, K. D. *PNAS*, 2002, 99, 5241-5246.) are incorporated in/on a sensing layer of an electrode, the bacterial spores can be recognized by a biospecific reaction which takes place between the biological recognition component and bacterial spores—without any pre-concentration or separation process.

In particular embodiments, bacterial spores (receptor) and peptide, which is fixed on the surface of substrate, associate in solution to form a peptide-spores biological complex. The residual potential due to complementarity between the peptide (the complementary ligand) and the bacterial spores (receptor) with the best possible electrostatic free energy change, is equal in magnitude and opposite in sign to the ligand desolvation potential everywhere within the ligand including on the ligand surface. (See, for example: Honig, B., Nicholls, A. *Science*, 1995, 268, 1144-1149; Honig, B., Sharp, K., Yang, A.-S. *J. Phys. Chem.*, 1993, 97, 1101-1109; Lee, L.-P., B. Tidor, B. *J. Chem. Phys.*, 1997, 106, 8681-8690; Chong, L. T., Dempster, S. E., Hendsch, Z. S., Lee, L-P., Tidor, B. *Protein Sc.*, 1998, 7, 206-210; and Kangas, E., Tidor, B. *J. Chem. Phys.*, 1998, 109, 7522-7545.) Under the electromotive force (potentiometry), the surface electrostatic potentials of the peptide-spores complex formed relates to the specific biorecognition process enabling bacterial spores to be identified and detected by potentiometry.

Many of the technologies developed and/or currently being used however, such as FT-IR spectroscopy, fluorescence spectroscopy, polymerase chain reaction (“PCR”), flow cytometry, impedimetry, UV resonant Raman spectroscopy, and others, are large, expensive, or require sophisticated, relatively time-consuming, and often extensive analysis procedures.

Accordingly, devices and methods which facilitate the accurate, quick, convenient and inexpensive detection of biological or other chemical agents are of significant scientific and societal interest.

In view of the limitations in the art, a flexible method for selectively detecting a wide range of molecules is needed. Additionally, it is desirable that such methods and devices constructed therefrom be applicable to the detection of biological or other chemical agents.

Such methods and devices are the subject of the instant invention.

§2. SUMMARY OF THE INVENTION

We have developed methods for fabricating biosensors, as well as several specific biosensors, suitable for the sensing/detection of biological or chemical agents of significant interest. Our inventive methods and sensors may involve the immobilization of biological and/or chemical recognition components (selectors or probes) on a substrate by using a polymer layer, such as a Polysiloxane Monolayer immobilization (PMI). The PMI method may be used to immobilize the selectors on the substrate by forming a physical bond between the monolayer and the selector (e.g., by adsorption).

In one embodiment, a monolayer of polysiloxane is polymerized on a substrate, onto which selector molecules are adsorbed. The resulting immobilized selector molecules may then be used to interact with specific molecules (targets) within a mixture of molecules, thereby enabling those specific molecules to be detected and/or quantified. Advantageously, selector-target interactions may be detected by a variety of methods and/or devices including, microscopy, quartz crystal microbalances (QCM)(gravimetric), acoustical, heat generation, conductivity, ion-sensitivity (e.g., ion-sensitive field-effect transistors), dielectric, magnetic or electrochemical devices such as potentiometers and potentiostats.

In addition, we have developed inventive biosensors, which may be fabricated according to the methods just introduced, which include two specific peptides for *B. subtilis* and *B. anthracis* Sterne. The peptides may be immobilized on (or otherwise coupled with) the surface of a substrate, such as indium tin oxide (“ITO”) glass plates, using a polymer layer, such as a polymer monolayer resulting from Polysiloxane Monolayer Immobilization ("PMI") technique. Such sensors may be employed to identify those *Bacillus* spores.

§3. BRIEF DESCRIPTION OF THE DRAWINGS

Further features and aspects of the present invention may be readily understood from the Drawing in which.

Figure 6:
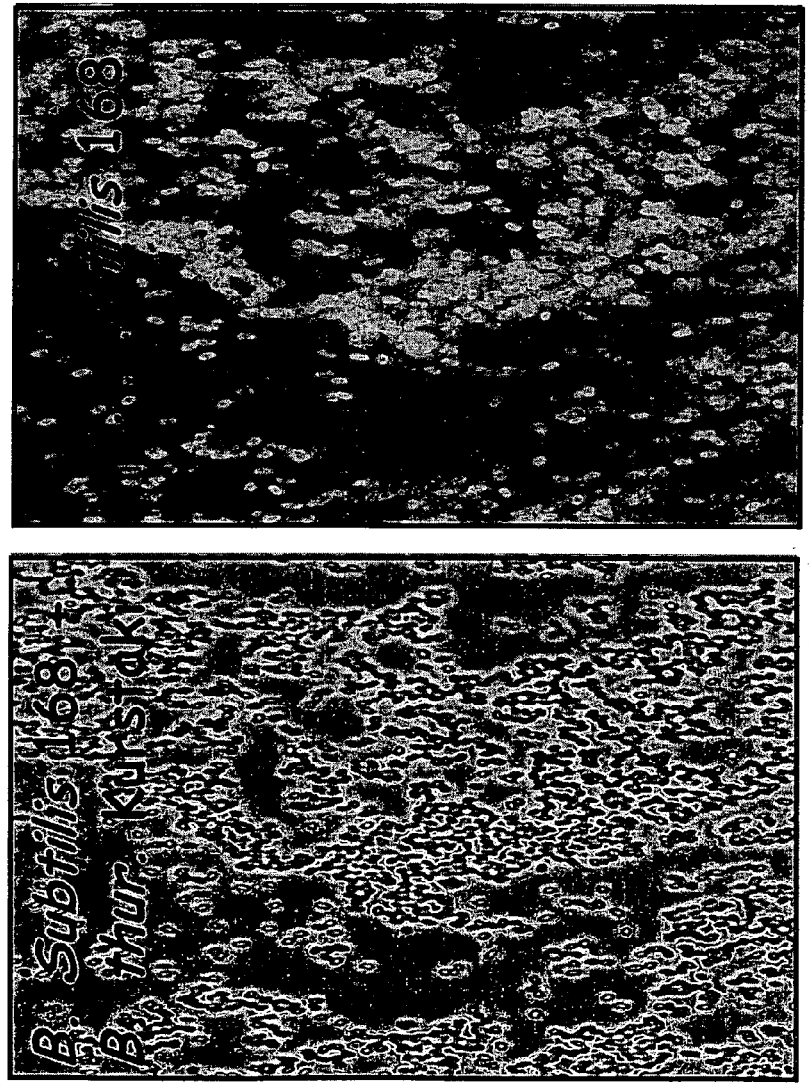

FIG. 6 includes a phase contrast microscopic image and fluorescence microscopic image of labeled spores.

Figure 7:
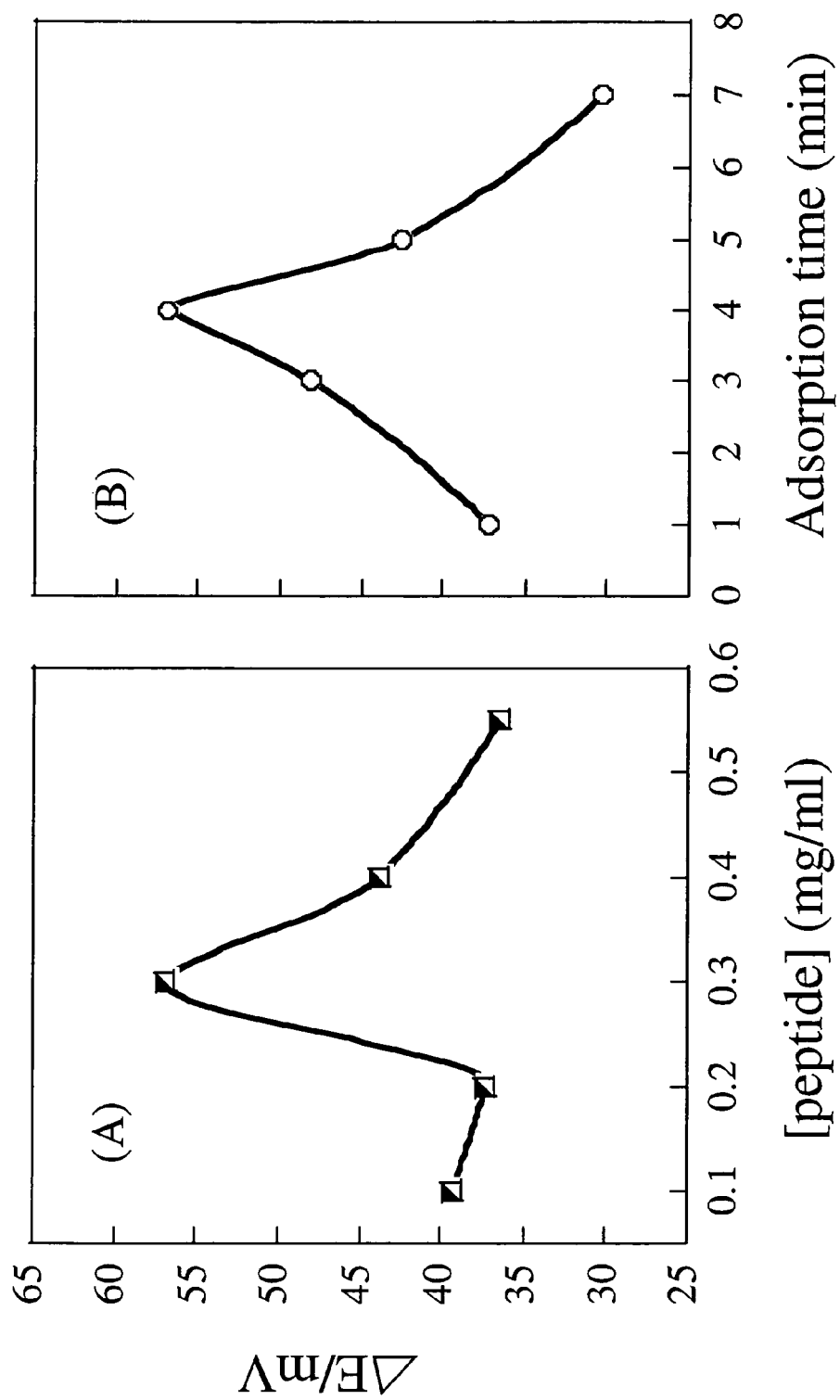
Figure 8:
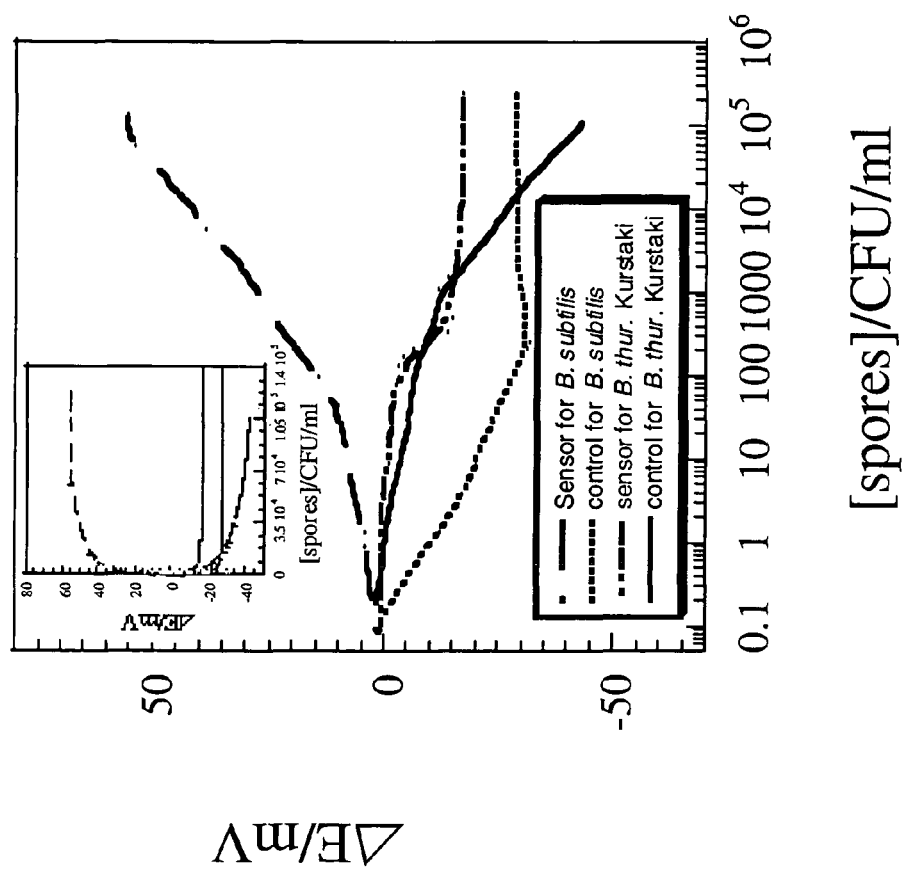
Figure 9A:
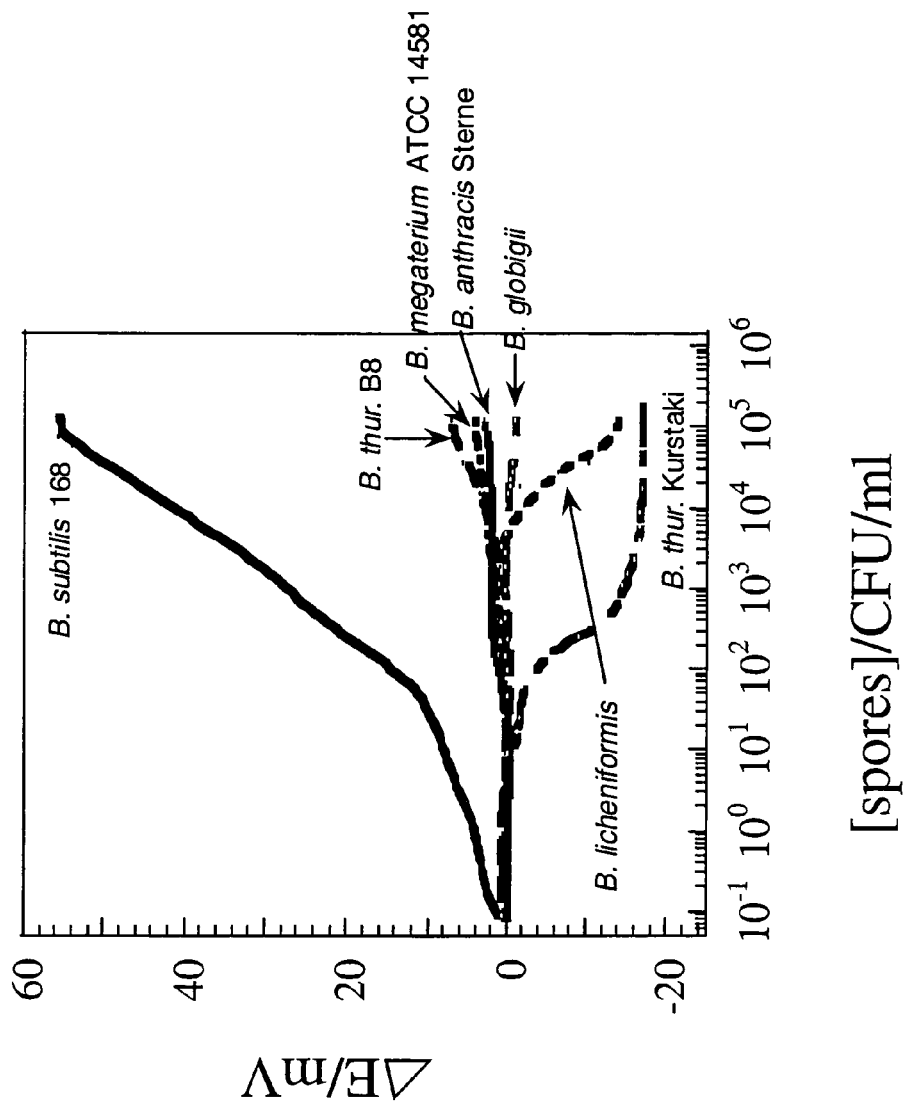
Figure 9B:
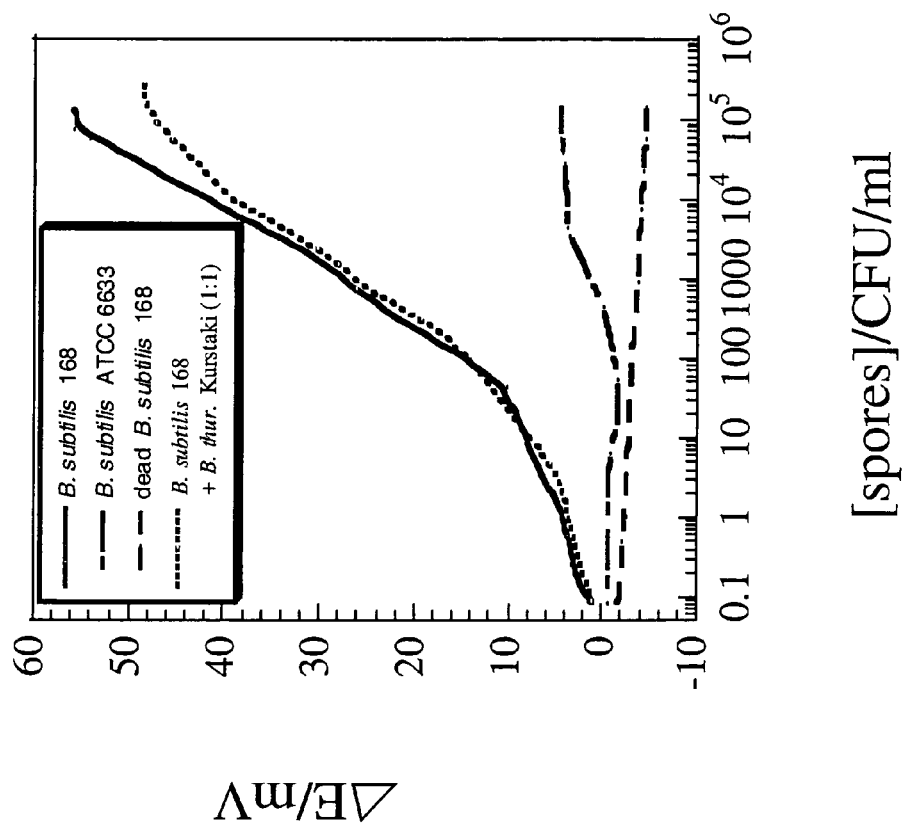
Figure 10:
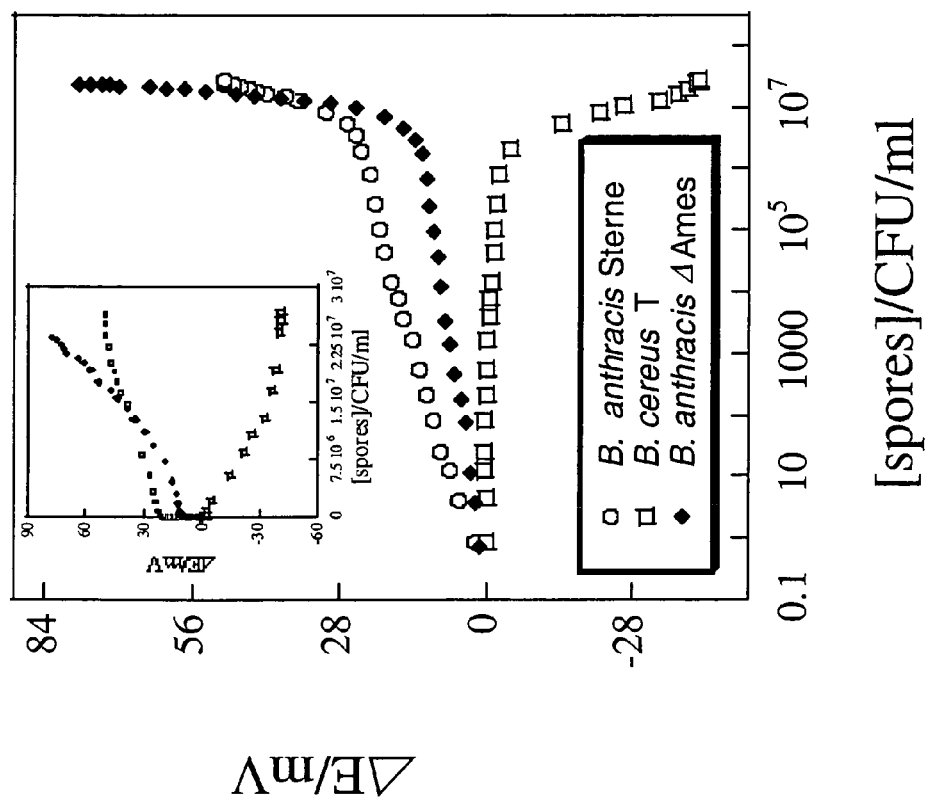
Figure 11:
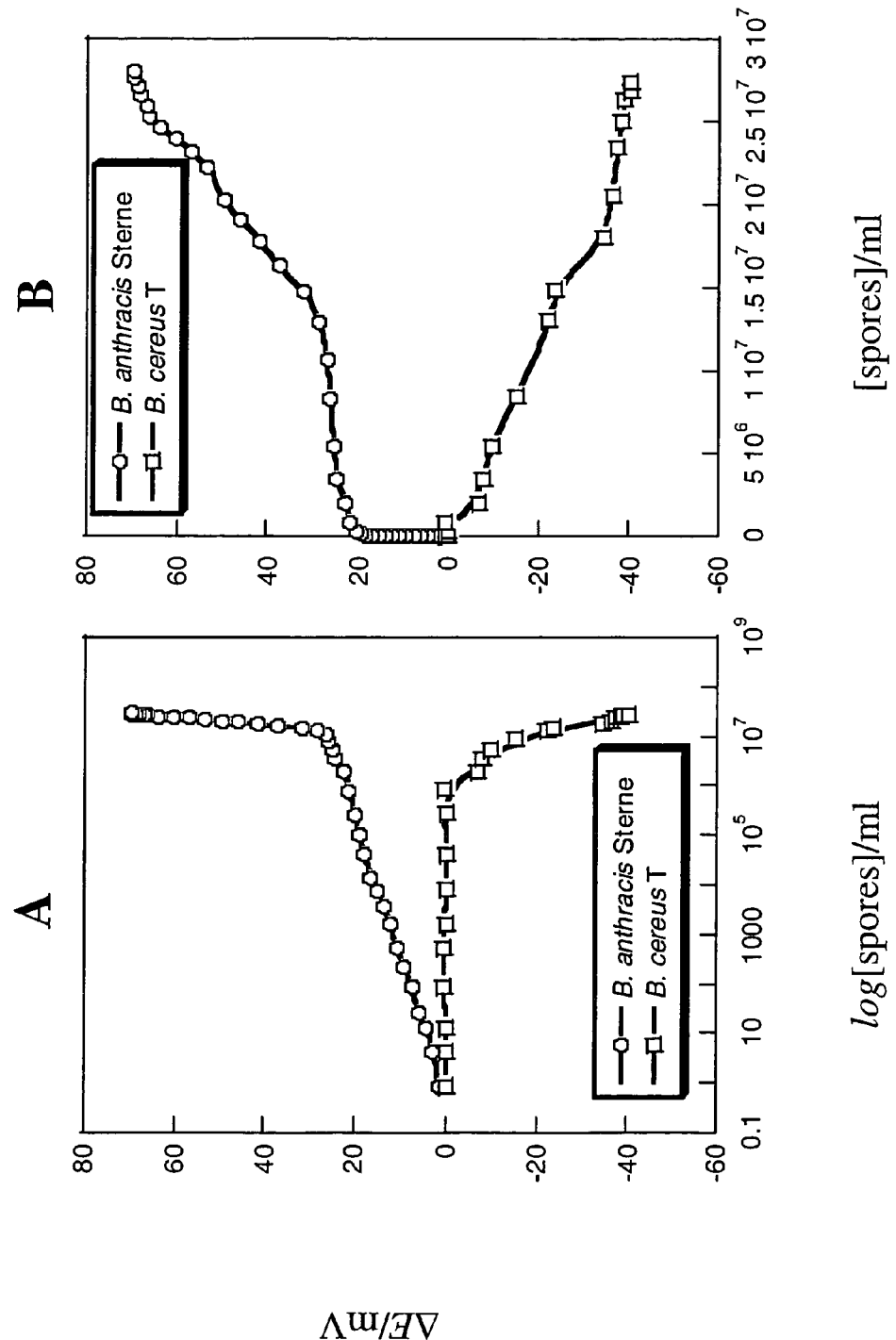

FIGS. 7(A) and 7(B) are graphs showing the influence of peptide concentration in the ODS-CHCl$_3$/CCl$_4$ deposition solution and the effect of the co-adsorption time on the potentiometric response of peptide/ODS ITO sensor;

FIG. 8 is a graph showing potentiometric responses of *B. subtilis* on ODA ITO electrodes with and without peptide and *B. thur*. Kurstaki with and without peptide;

FIGS. 9(A) and 9(B) are graphs showing (A) potentiometric responses of peptide/ODA ITO sensor to other kinds of spores and (B) *B. subtilis: B. thur*. Kurstaki;

FIG. 10 is a graph showing potentiometric responses of peptide for *B. anthracis* Sterne; *B. cereus* T; and *B. anthracis* Ames; and FIGS. 11(A) and 11(B) are graphs showing potentiometric responses of polylysine/ODS sensors to *B. anthracis* Sterne and *B. cereus* T using (A)log [spores]/ml and (B)[spores]/ml.

§4. DETAILED DESCRIPTION

The following description is presented to enable one skilled in the art to make and use our invention, and is provided in the context of further particular embodiments and methods. The present invention is not limited to the particular embodiments and methods described.

Polysiloxane monolayer immobilization methods are described in §4.1. Exemplary conditions for the preparation of our inventive biosensor(s), as well as measurements of the properties of experimental bio-sensor(s), are described in §4.2. Finally, exemplary peptide/ODS biosensors are described in §4.3 for *B. subtilis* spores and *B. anthracis* Sterne.

§4.1 Performing Polysiloxane Monolayer Immobilization

Our inventive immobilization methods generally involves: (1) polymerizing a layer of polysiloxane onto a substrate, and (2) allowing selector molecules to be physically adsorbed to (or coupled via one or more intermediate elements with), or otherwise immobilized on the substrate using the polymer layer. The polymerizing and selector molecule immobilization may occur substantially concurrently. The resulting polymer/selector-coated substrate can then be dried and washed, if necessary.

Polymerizing to obtain a polymer layer with selector molecules immobilized in/onto it generally involves soaking a substrate in a suspension of selectors in solvent containing polysiloxane-forming monomers. After drying and washing, a template may be adsorbed onto the polysiloxane layer on the support surface and held in place by hydrophobic silanol groups.

The substrate used in PMI acts as a support surface for the polymer layer. Advantageously, substrate choice(s) largely depend on the method used for detecting interactions between immobilized selectors and target molecules in solution. For example, if potentiometry is used as the detection method, an electrode may be used as the substrate. If microscopy is used as the detection method, a microscope slide may be used as the substrate. As a result, and as can be readily appreciated by those skilled in the art, our inventive methods and sensors constructed according thereto accommodate a wide variety of substrates and detection techniques (such as microscopy, quartz crystal microbalance, or gravmetric, acoustic, heat generation, conductivity, ion-selectivity, dielectric, magnetic, electrochemical, etc.). Additional sensory substrates may include solid-state electronic devices such as diodes or transistors including insulated gate field effect transistors (IG-FETs), metal oxide semiconductor field effect transistors (MOSFETs) and field effect transistors (FETs).

In one preferred embodiment, polymers used in PMI are covalently bound to the substrate's surface. Therefore, the substrate's molecular structure includes atoms that can bind the polymer monomers on the substrate's surface. An exemplary embodiment of our invention uses an indium-tin oxide (ITO) glass electrode as the substrate. As can be appreciated by those skilled in the art, covalent bonding of the polymer to the substrate surface is not required, however, as any type of mechanical/chemical/electrostatic or other bonding is acceptable, so long as it is sufficiently durable and does not negatively interfere with detection.

Although polysiloxane-forming monomers are described, as can be appreciated by those skilled in the art, other polymer-forming monomers may be used to generate a polymer layer to immobilize the selector molecules with respect to the substrate.

Figure 1:
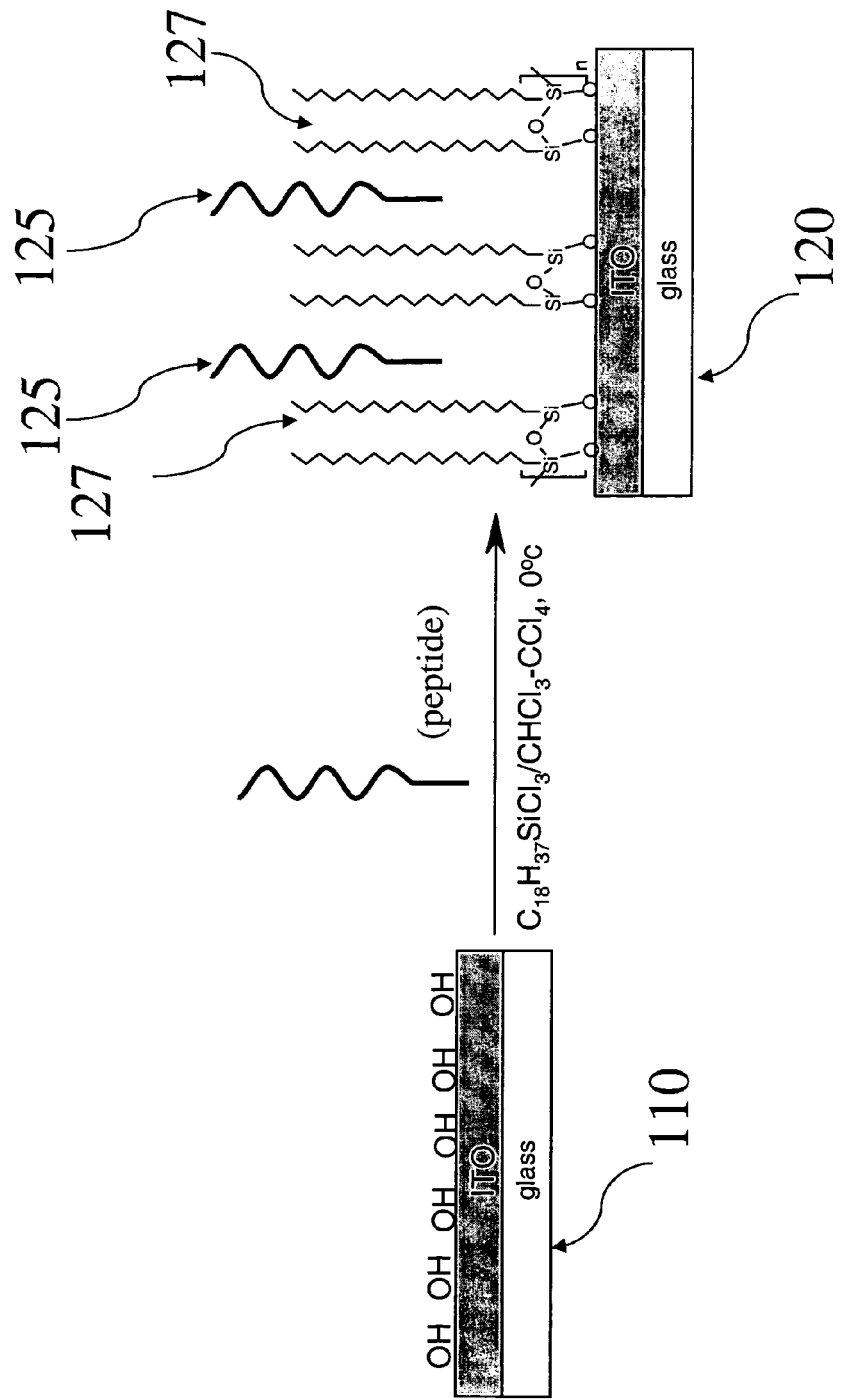
FIG. 1 is a diagram depicting PMI fabrication of a peptide/ODS sensor for bacterial spores.
Figure 2:
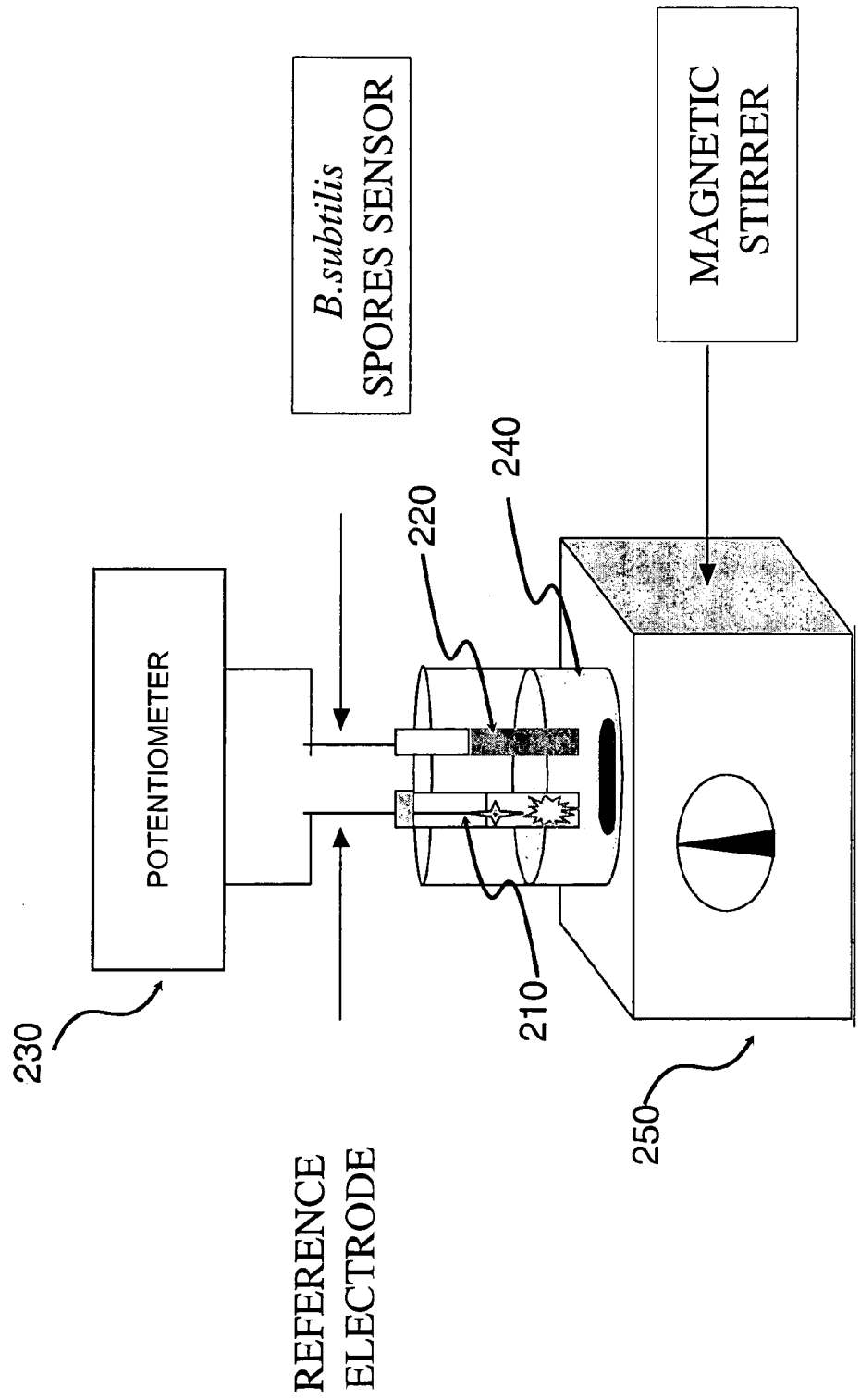
FIG. 2 is a diagram depicting the experimental assembly for detecting *B. subtilis* spores using potentiometry and a peptide/ODS sensor.

With reference now to FIG. 1, there is shown in schematic form a diagram depicting PMI fabrication of a peptide/ODS sensor for bacterial spores.

More specifically, and as shown in FIG. 1, treating the ITO electrode 110 with NaOH replaces OH groups with ONa groups resulting in modified ITO electrode 120. Such modification generally facilitates covalent binding of octadecyltrichlorosilane ($C_{18}H_{37}SiCl_3$) to surface oxygen atoms by displacing Na.

With continued reference to FIG. 1, the modified ITO electrode 120 is treated with a solution containing peptide, $C_{18}H_{37}SiCl_3$, CHCl$_3$, and CCl$_4$, at substantially 0° C., which results in polymer-modified ITO electrode 130 containing selector peptide 135 adsorbed onto the polymer monolayer.

As can be appreciated, the polymer monolayer functions to hold selector molecules in place. All-trichlorosilane compounds, such as octenyltrichlorosilane, cyclohexlmethyltrichlorosilane, bromopropyltrichlorosilane, trichlorosilane, tert-butyltrichlorosilane, ethoxytrichlorosilane, methyltrichlorosilane, pentyltrichlorosilane, etc., which could produce a polysiloxane monolayer are suitable polymers for PMI. Further, other molecular imprinting polymers (such as those prepared with protected amino acid benzyloxycarbonyl-L-tyrosine and either 2-vinlpyridine, acrylic, (4-vinylphenyl)boronic acid, vinylbenzoic acids, acrylamido-sulfonic acids, amino-methacrylamides, vinlpyridines, vinylimidazoles, acrylamides, vinyl-imminodiacetic acids, or methacrylic acid, or a combination of both, or some other self-assembly imprinting polymer avoid the need to use the washing step for removing the template, and therefore may be considered alternative polymers for PMI.

Selector molecules are physically adsorbed onto the substrate and held in place by hydrophobic silanol groups. Selector molecules may be held to the polymer layer, thereby immobilizing them on the substrate, in other ways. As a result, many biological or chemical materials may be used as selector molecules with our inventive PMI methods. More specifically, PMI selectors may include large biomaterials such as peptides, proteins, enzymes, antibodies, lectins, aptamers or nucleic acids, cells, bacterial tissues, receptors, and other kinds of biological and chemical molecular recognition elements. Additionally, selectors may be hydrophobic or hydrophilic, cationic or anionic, and may be biologically active. Furthermore, other elements and/or structures may exist between the selector molecule(s) and substrate. (See, e.g., U.S. Provisional application Ser. No. 06/370,502 (incorporated herein by reference), titled "DENDRIMER SENSOR FOR *BACILLUS SUBTILIS* SPORES," filed on Apr. 5, 2002.

§4.2 Experimental Procedures for Sensor Development and Evaluation

Experimental

Chemicals and Biochemicals

Chloroform and carbon tetrachloride were distilled over $CaH_2$. Other chemicals were used without further purification. Peptides were purchased from Advanced ChemTech, Inc (Louisville, Ky.). ALEXA FLUOR® 488, a fluorescent dye, was obtained from MOLECULAR PROBE® which is a brand of Life Technology Corporation (Eugene, Oreg.). All aqueous solution was prepared from water purified using MILLIPORE® System (Resistivity: 18.2 MΩ cm) and sterilized by autoclaving.

Bacterial Spores

Figures 3A, 3B:
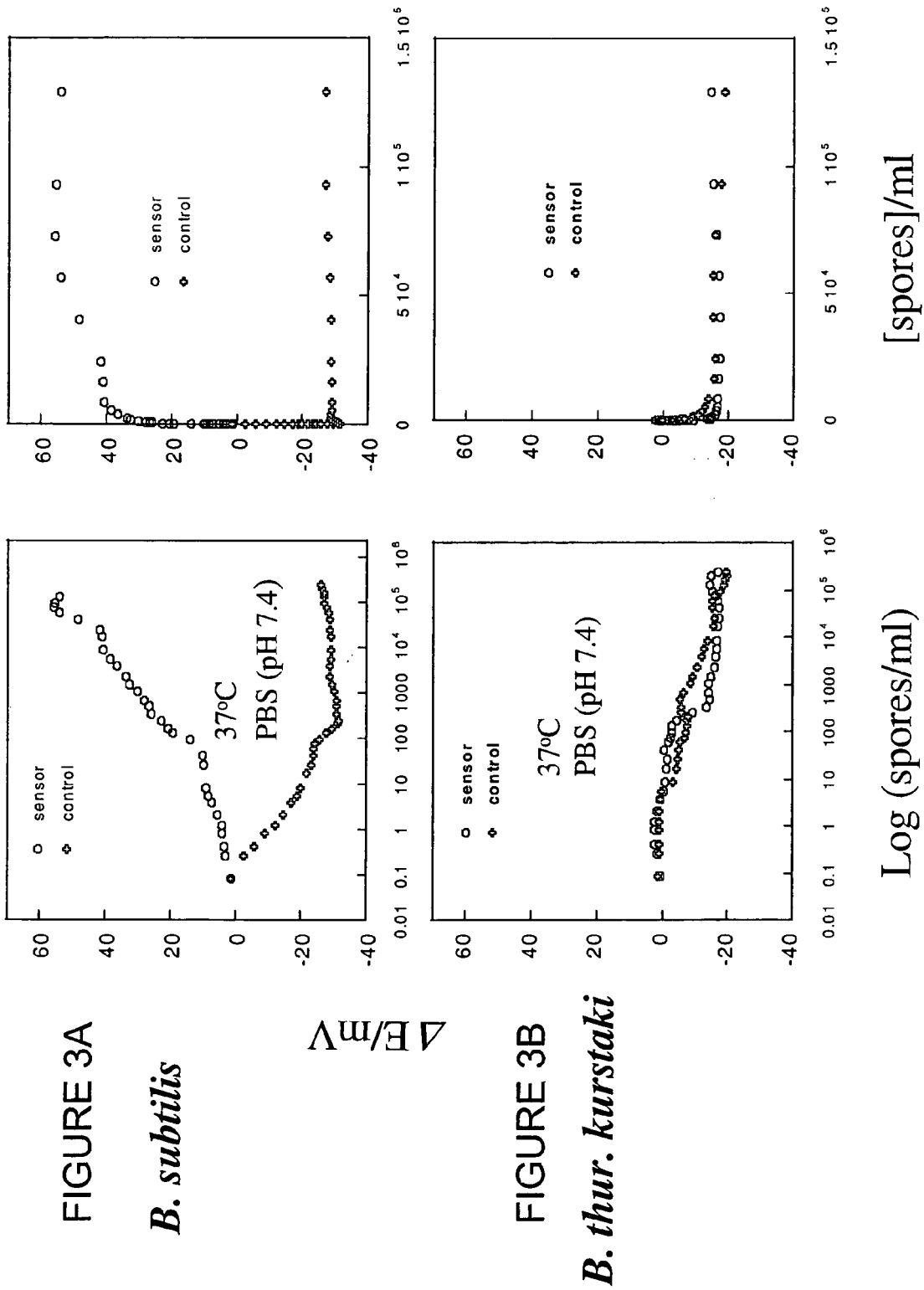
FIGS. 3a and 3b are graphs showing the potentiometric response of peptide/ODS sensor to *B. subtilis* and *Bacillus thurigiensis* kursaki spores, respectively.

*Bacillus subtilis* 1A700 (*B. subtilis*), *B. thuringiensis* Kurstaki (*B. thur.* Kurstaki), *B. thuringiensis* B8 (*B. thur.* B8), *B. licheniformis, B. globigii, B. anthracis* Sterne, *B. anthracis* ΔAmes, *B. cereus* T, and *B. megaterium* ATCC 14581 were grown in our laboratories. *B. subtilis* ATCC 6633 was purchased from Raven Biological Laboratories (Omaha, Me.).

Indium Tin Oxide (ITO) Electrodes and Surface Modification

ITO-coated glass (CG-50IN-CUV), which had a surface resistance of 10 $\Omega/cm^2$ was purchased from Delta Technologies (Stillwater, Minn.). The substrates were cleaned with concentrated nitric acid, 0.02 M sodium hydroxide, and water, respectively. Before the modification, the substrates were dried under a stream of nitrogen. They were subsequently (effective surface area about $1\times4$ $cm^2$) immersed into a solution of 2:3 (v/v) $CHCl_3/CCl_4$ suspension containing octadecyltrichlorosilane (ODS) ($8\times10^{-4}$ M) and peptide (0.30 mg/ml) at 0° C. for four minutes. The electrode was allowed to stand overnight at −20° C. Then peptide sensors were washed with water to remove the un-immobilized peptide from the surface and ready for use. ODS modified electrode without the peptide was also prepared as a control.

Microscope Imaging

All microscope experiments were performed on a fluorescence Microscope. NIKON ECLIPSE® E600 (Diagnostic Instruments, Inc.). $7.2\times10^5$ CPU/ml *B. Subtilis* spores were labeled with ALEXA FLUOR® and then mixed with the same amount of unlabeled *B. thur*. Kurstaki spores. A 1 μL mixture of the above spores was added to the surface of peptide/ODS sensors (or the control), and checked under both phase-contrast and fluorescence microscope. They were checked under the microscope again after incubating 10 minutes and washing thoroughly using sterile water to remove non-captured spores.

Electrochemical Measurement

Potentiometric experiments were performed with an ORION® 920A Potentiometer. All measurements were made in 50 ml of pH 7.4 PBS buffer thermostated to 37° C., in a 100 mL working volume single-compartment electrochemical cell (EG&G), equipped with magnetic stirrer. The two-electrode system included an Ag/AgCl (saturated KCl) reference electrode and the peptide/ODS/ITO sensor (or the control) working electrode. Thereafter, the potential response of the sensor was defined as the difference between the electrode potential with and without bacterial spores in solution, i.e., $\Delta E=E_1-E_0$, where $E_0$ and $E_1$ are the electrode potentials before and after the addition of bacterial spores, respectively.

§4.3 Sensors for *B. Subtilis* Spores and *B. Anthracis* Sterne

As can now be readily appreciated, our inventive PMI methods of immobilizing a selector molecule on a support surface have significant implications for sensor development. More specifically, PMI may be used to immobilize a selector on the surface of an electrode, creating a sensor that selectively recognizes a molecule that interacts with the selector. We have applied our invention to the fabrication of novel sensors for selectively detecting bacteria, amino acids, and target DNA.

In an exemplary embodiment of our inventive PMI methods, a PMI-modified sensor was developed for recognizing *Bacillus subtilis* spores and *Bacillus Anthracis*. Advantageously, and unlike indirect sensors which are responsive to products of degraded spores (such as those produced by molecular imprinted polymers, e.g., dipicolinic acid), our inventive PMI-modified sensors are direct sensors in that they are responsive to intact spores.

To fabricate a bacterial sensor, and in particular the *B. subtilis* spores sensor, an ITO glass electrode may be used as the substrate and Peptide may be used as selectors. Treating the ITO glass electrode with NaOH replaces surface OH groups with ONa groups. The ITO glass electrode may then be coated by soaking it in a suspension of peptide selector molecules (~0.35 mg/ml) and $CHCl_3/CCl_4$ (a volume ratio of 2:3) containing 0.8 mM ODS for approximately four minutes. The selector/polymer-coated electrode is then dried overnight and then washed with water.

With further reference to FIG. 1, and as shown therein, the peptide 135 is immobilized between carbon chains on the ODS monolayer 137 using this fabrication method. Note further that the template was not washed out with water since the hydrophobic layer prevents water from approaching the template. A low polarity medium such as chloroform, however, may remove the template from the monolayer.

FIG. 2 shows an experimental assembly 200 of *B. subtilis* spore detection using potentiometry and a PMI-modified sensor. The detection assembly 200 includes a reference electrode 210 and the *B. subtilis* spore sensor 220, both attached to a potentiometer 230. In this configuration, the reference electrode 210 and sensor 220 are suspended in a solution 240 containing *B. subtilis* spores stirred by a magnetic stirrer 250. With this detection assembly 200, the specific interaction between immobilized peptide on the surface of the sensor 220 and *B. subtilis* spore, produces an electrochemical event which may be measured by potentiometry.

To test the specificity of our inventive peptide/ODS sensor to *B. subtilis* spores, its detection, versus that of a control (e.g., a blank sensor) detection, of *B. subtilis* and *B. thur*. kursaki spores was measured. FIG. 3A shows the sensitivity of the *B. subtilis* peptide/ODS sensor, and the insensitivity of the blank sensor, to *B. subtilis* spores. Advantageously, and as expected, neither sensor was sensitive to *B. thur. kursaki* spores, as shown in FIG. 3B.

Figure 4:
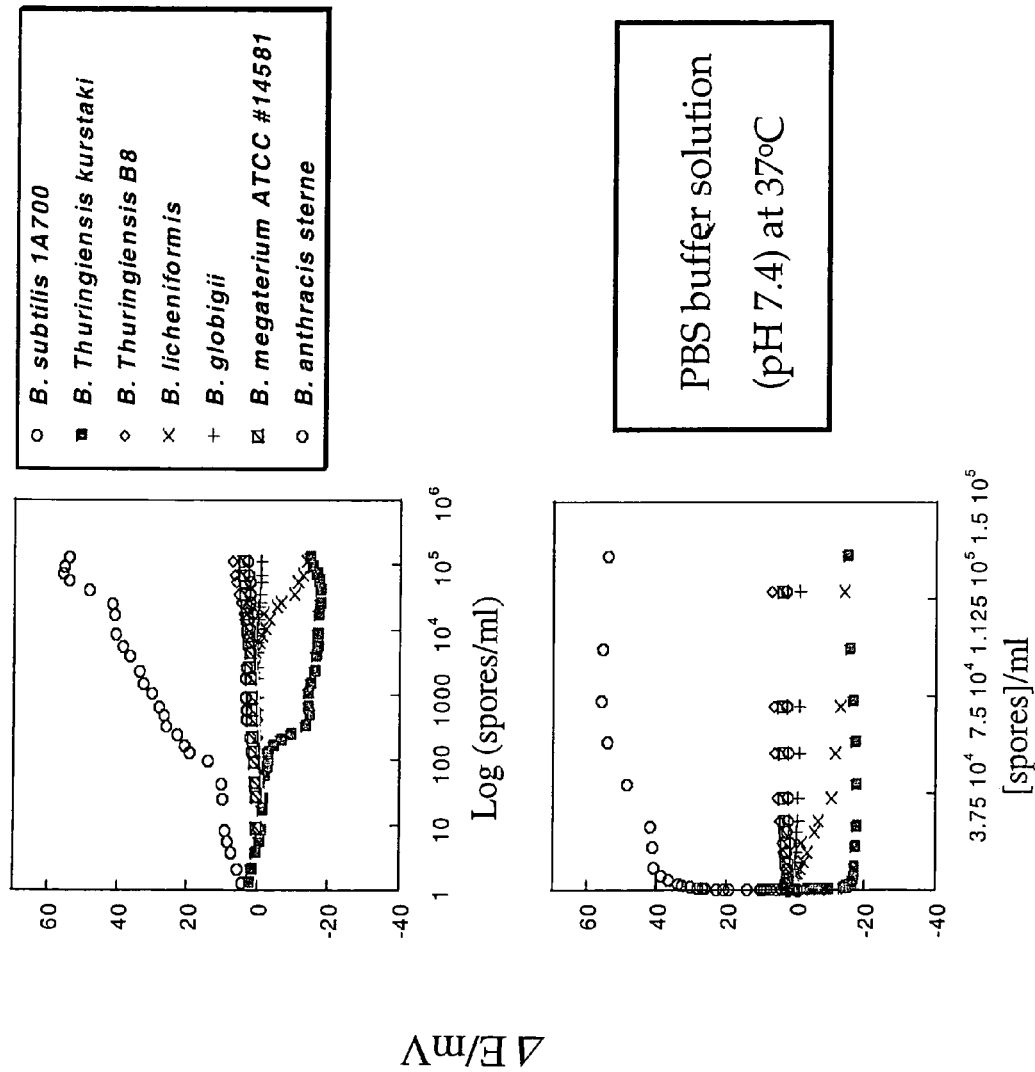
FIG. 4 is a graph (shown as both log concentration and concentration) showing the potentiometric responses of other kinds of spores on peptide/ODS sensors.

Similarly, FIG. 4 shows the insensitivity of the *B. subtilis* peptide/ODS sensor to various bacteria spores other than *B. subtilis* spores. These results demonstrate the high selectivity of the PMI-modified sensor to its target molecule.

Figure 5:
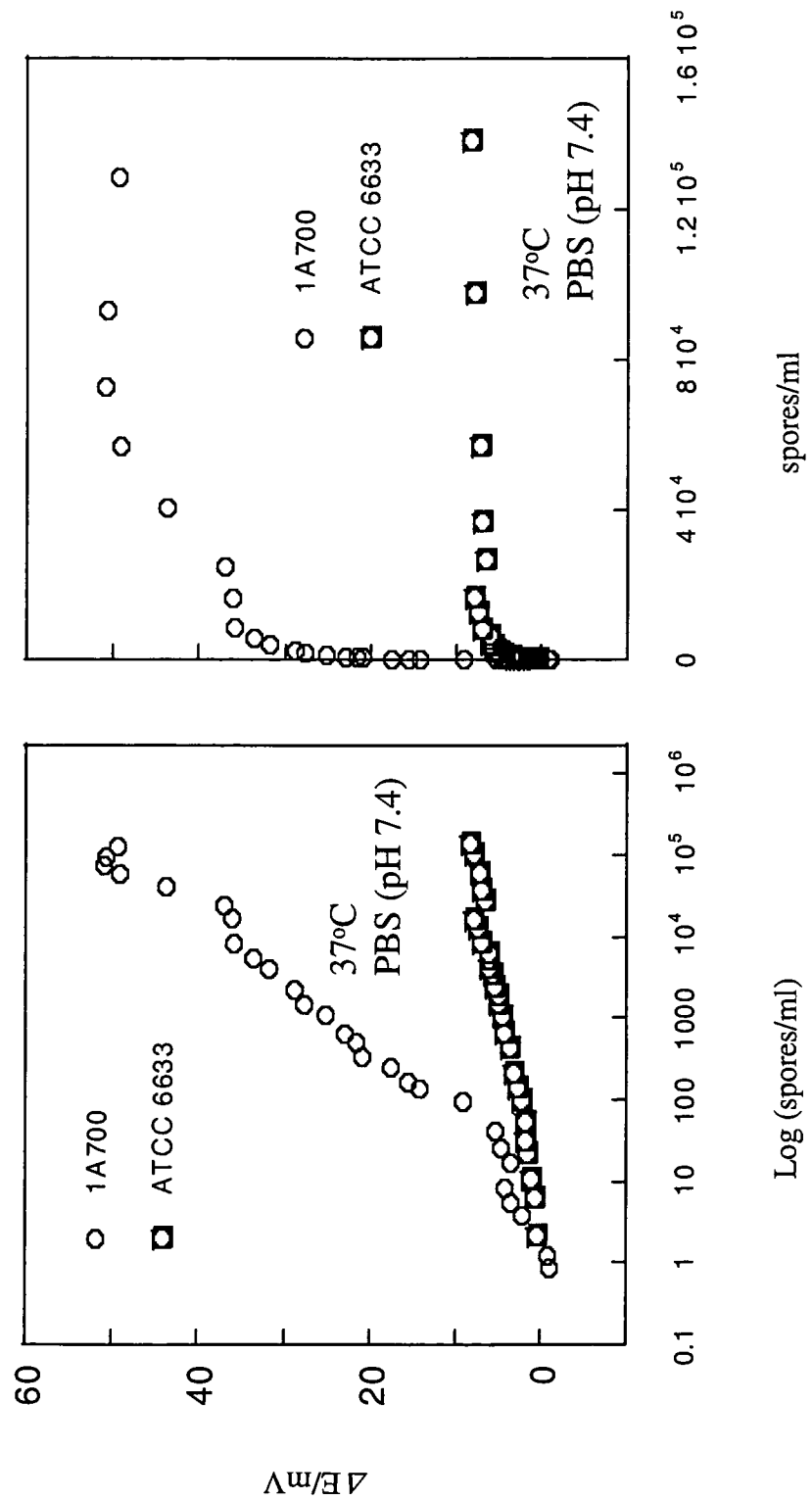
FIG. 5 is a graph (shown as both log concentration and concentration) showing the potentiometric responses of peptide/ODS sensors of *B. subtilis* strain 1A700 and *B. subtilis* ATCC 6633, respectively.

Of further advantage, our inventive peptide/ODS sensor is sensitive to even a particular strain of *B. subtilis* spores. Turning our attention now to FIG. 5, it can be seen that our inventive sensor only identified the strain of bacteria (1A700) for which its immobilized peptides were specific. A different strain (ATCC 6633) went largely undetected by the sensor.

To further evaluate our inventive method and sensors, two heptapeptide ligands that bind species-specifically to spores of selected *Bacillus subtilis* and *anthracis* Sterne species were identified by Phase Display (Ph.D.) Ligand Screening System. These peptides were immobilized on the surface of ITO glass by Polysiloxane Monolayer Immobilization (PMI) in a manner as previously described.

As described before and now stated alternatively, PMI is a novel method to immobilize chemical or biological molecular recognition elements (probe or ligand) on substrates. Basically, ligand (in this example, peptide) and the silylating agent (ODS) were co-adsorbed on the polar solid surface of the ITO glass plates, the ligand was incorporated into a polysiloxane monolayer by forming a hydrophobic layer of polymerized organosiloxane groups around the molecule recognition elements as depicted in FIG. 1.

The chemical or biological recognition ligand was dissolved or suspended in a low polarity medium during immobilization. The ligand could not be removed with water since the hydrophobic polymer monolayer prevents water from approaching the ligands, even though most of the ligands are water soluble. This may be due to the hydrophobic layer preventing water approach to peptide, which was surrounded by aliphatic chain. Therefore, the resulting immobilized ligand may then be used to interact with specific chemical or biological targets within a mixture of molecules, thereby enabling specific analyte to be detected and/or quantified.

To find the optimal biorecognition conditions, the influences of the peptide concentration in the deposition solution and co-adsorption time during the fabrication of the sensors were examined. When the concentrations of peptide concentration ranging from 0.1 to 0.55 mg/ml in $CHCl_3/CCl_4$—ODS solution, the potentiometric output of those sensors is shown in FIG. 7(A). When the concentrations of peptide is 0.30 mg/ml, the resulted sensor produced the highest potential responses to $1.3\times10^5$ CFU/ml *B. subtilis* spores in $1.0\times10^{-2}$ M phosphate buffer—$1.5\times10^{-1}$ M NaCl (PBS buffer, pH 7.4). After the immersion of the pretreated ITO-coated plates into the solution containing ODS and peptide for time periods varying from 1 to 7 minutes, the potential responses of these electrodes were observed at *B. subtilis* spores concentrations ranging from 0.08 to $2.0\times10^5$ CFU/ml *B. subtilis* spores. The peak response was observed at an immersion time of approximately 4 minutes, as shown in FIG. 7(B).

The influence of incubation temperature was also investigated since it cannot be guaranteed that 37° C. will be the temperature when the sensor is used in field. At 28.5° C., the signal remains 97.7% of that produced at 37° C., and 48.6% of that produced at 23° C. Incubation temperature has a marked influence on biorecognition process and those devices can still be used at around 25° C.

In FIG. 8, curve (----) is control (without peptide) towards *B. subtilis*. As the concentration of *B. subtilis* increases, potential output decreases. When the concentration of *B. subtilis* is 500 CFU/ml, the potential found with the control does not decrease further, and stabilizes. This characteristic indicates that *B. subtilis* has strong negative charge. However, when the peptide is immobilized in the selective layer of the sensor, the results (FIG. 8, curve (———)) demonstrated potential change in a direction opposite to that without peptide (FIG. 8, curve (----)). The potential response of the sensor to the *B. subtilis* spores in a PBS suspension was linear in the concentration range of $0.08$-$7.3\times10^4$ CFU/ml and the limit of detection (LOD) was 0.08 CFU/ml.

The distinctive difference in the potential outputs can be observed before and after immobilizing the peptide onto the active surface of ITO. This phenomenon indicates that peptide was successfully linked to the ITO surface. Peptide ligand (7 amino acids long) containing the consensus sequence NHFLP binds tightly, and species specifically, to spores of *B. subtilis* and forms a complex. This peptide—*B. subtilis* complex carries positive charge, which is totally different from the spores themselves (FIG. 8, curve (----)).

*B. thur.* Kurstaki spores were used to evaluate the binding of other kind of spores to the peptide/ODS surface. Curve (———) and curve (- - ———) in FIG. 8 were potential response of a control (without peptide) sensor and a peptide sensor (with peptide) to *B. thur.* Kurstaki spores, respectively. Results obtained show that negative charge of *B. thur.* Kurstaki spores did not change after they encountered peptide. In other words, the peptide did not have any significant affinity for *B. thur.* Kurstaki spores.

In the case of *B. subtilis*, the peptide ligand appears to mimic the binding of the SpsC protein. This protein apparently binds to the surface of the forespore and may be required for the synthesis of surface polysaccharides late in the spore development. Polysaccharide deposition apparently causes *B. subtilis* spores to be hydrophilic. Genetic inactivation of the operon encoding SpsC causes *B. subtilis* spores to become hydrophobic much like spores of *B. anthracis*. Accordingly, *B. subtilis* Δsps spores may provide an improved simultant for spores of *B. anthracis*.

Optical microscopy was also used to evaluate the binding of bacterial spores to the surface-confined peptides. A representative image of peptide sensor after reaction with $1.44\times10^6$ mixture of same amount of *B. subtilis* and *B. thur.* Kurstaki spores on the surface is shown in FIG. 6. Both spores were observed under phase contrast. However, only *B. subtilis* spores could be seen under fluorescence as they are labeled with fluorescence reagent, Alexa 488. Images obtained at several different locations on the surface show that the selectivity of the immobilized peptide to *B. subtilis* is 98%, due to the very similar pictures of the same sensor under phase contrast and fluorescence microscope.

As can be appreciated, effective testing of bacteria requires methods of analysis that meet a number of challenging criteria. Selectivity and time of analysis are important characteristics related to the usefulness of microbiological testing. The biosensor system should have the specificity to distinguish the target bacteria or bacterial spores from others. FIG. 9(A) shows the potentiometric output in pH 7.4 PBS buffer upon treatment of sensing interface with same amount ($2.5\times10^5$ CFU/ml) but different kinds of bacterial spores. The data of potentiometric measurement in the inset figure in FIG. 9(A) can be simulated with Nicolsky-Eisenman Equation:

$$E = E^0_{B.subtilis} + s\log([B.subtilis] + K^{POT}_{B.subtilis,j}[a_j^{zj}]) \quad (1)$$

where $E_{B.subtilis}$ and $E_{B.subtilis}{}^0$ are the potential of the sensor and the standard electrode potential, respectively, s is the slope. $K_{B.subtilis,j}^{POT}$ (j, interference of charge $z_j$) was obtained for peptide biosensor based on simulation results of the experimental data shown in FIG. 9(A), and shown in Table 1.

TABLE 1

Potentiometric selectivity coefficients

| Spores | B. thur. Kurstaki | B. licheniformis | B. thur. B8 | B. globigii | B. megaterium ATCC 14581 | B. anthracis Sterne |
|---|---|---|---|---|---|---|
| $K_{B.subtilis,j}^{POT}$ | 0 | 0 | $1.0 \times 10^{-5}$ | 0 | $2.5 \times 10^{-6}$ | $12.5 \times 10^{-9}$ |

Besides B. subtilis, none of those bacterial spores produced any false positive potentiometric response, implying that the peptide is specific for B. subtilis.

The high selectivity of our inventive biosensor also reflects in the identification of B. subtilis in the presence of other bacterial spores, e.g., B. thur. Kurstaki spores (FIG. 9(B) (blank line)). The results indicate that the sensor has almost the same potential response in the presence of the equal amounts of the B. thur. Kurstaki at concentration ranges from 0.08 to 9000 CFU/ml. No substantial potential difference was observed with and without B. thur. Kurstaki, which demonstrates a high degree of selectivity. The biosensor could distinguish B. subtilis from other strains of the same species, such as B. subtilis ATCC 6633 (FIG. 9(B) (- - -), which strain is different from B. subtilis 1A700. In the presence of $1.3 \times 10^5$ CFU/ml, the biosensor gives 55.8 mV to B. subtilis 1A700 and only 4.6 mV for B. subtilis ATCC 6633 demonstrating highly selective of the peptide/ODS sensor. Advantageously, even live and dead spores can be distinguished from one another. As demonstrated in FIG. 9(B), (-- --), as B. subtilis 1A700 gave no more positive potential response after autoclaved.

Following the same facile modification of patterning and assay procedures, another kind of inventive peptide/ODS biosensor was developed for the detection of B. anthracis Sterne spores.

As was the case with B. subtilis, this peptide sequence binds tightly and species specifically to spores of B. anthracis Sterne solution ranging in concentration from 0.8 to $2.5 \times 10^7$ CFU/ml and forms a positive potential response complex.

With reference now to FIG. 10, there is shown a graph depicting potentiometric responses of sensors for anthrax spores constructed according to our inventive teachings for ODI/peptide for B. anthracis Sterne; B. cereus T; and B. anthracis Ames. As can be readily appreciated, the response is quite specific to the anthrax spores.

As can be seen by inspection of FIG. 10, B. cereus T (FIG. 10 (□)), which is very similar to B. anthracis Sterne, is undetected by our ODI/peptide sensor. And while both kinds of spores demonstrated binding by FACS analysis, potentiometric measurement advantageously provides the bias for the discrimination between B. anthracis Sterne and B. cereus T.

Additionally, the same sensor was employed to identify B. anthracis ΔAmes, which should have more affinity for this peptide than B. anthracis Sterne, as shown in FIG. 10 (♦)). As is shown in FIG. 10, when the concentration of bacterial spores $<10^7$ CFU/ml, B. anthracis Sterne produced a highly potentiometric output than B. anthracis ΔAmes, but when $>10^7$ CFU/ml, the sensor yielded higher affinity of the peptide for B. anthracis ΔAmes than B. anthracis Sterne.

Lastly, and as mentioned earlier, there are a number of chemical or biological molecular recognition elements (probe or ligand) that may be immobilized on suitable substrates and used to provide chemical/biological specificity to a sensor. FIGS. 11(A) and 11(B) show graphs of such specific sensors.

As noted before, ligand (in this example, polylysine) and the silylating agent (ODS) were employed. The resulting immobilized ligand (polylysine) was then be used to interact with specific chemical or biological targets, thereby enabling specific analyte to be detected and/or quantified. With reference to FIGS. 11(A) and 11(B), there is shown potentiometric measurements of B. anthracis Sterne and B. cereus T shown in both log [spores]/ml and [spores]/ml. As can be readily appreciated by those skilled in the art, our inventive methods and resulting devices are capable of providing a wide array of specific sensors and may include, for example, synthetic molecules that exhibit specific binding.

§5. CONCLUSIONS

Sensors and methods of fabricating same for the detection and identification of biological or other chemical agents, and in particular bacteria, so far are characterized by a lengthy analysis time. The assay time is usually on the order of several tens of minutes to several hours, even days. For our inventive peptide/ODS sensor, the time required to obtain equilibrium and incubation is five (5) minutes for a single test. Consequently, the biospecific reaction between, for example, B. subtilis spores and peptide is directly determined in real time by measuring the potentiometric changes induced by the complex formation between peptide and B. subtilis spores. Our inventive sensors and method of making same offers the potential to speed up the detection of anthrax and other pathogenic bacteria.

Additional problems facing the production of biosensors for direct detection of bacterial spores include the sensitivity of assay in real samples, long lifetime of the sensor and non-specific adsorption. With our inventive sensors, the limit of detection (LOD) is on the order of 8 CFU/100 ml, as described above, which is much improved compare to existed techniques.

Still further, after being stored at −20° C. in a freezer for several months, the response still remained to 40% of its initial magnitude, demonstrating the long lifetime of our inventive sensors.

Various modifications to the disclosed embodiments and methods will be apparent to those skilled in the art, and the general principles set forth may be applied to other embodiments, methods and applications. Thus, the present invention is not intended to be limited to the embodiments and methods. For example, although various embodiments of the invention were described in the context of sensing biological material, the teachings of the present invention can be applied to sensing other substances, such as chemicals. Additionally, our inventive teachings should be read to include a broad array of immobilization techniques, in which a bio-active material is brought together with sufficient monomer, such that when the monomer polymerizes on a suitable substrate, the bio-active material becomes sufficiently immobilized within the polymer to create a bio-active layer(s) on the surface of the substrate. When the substrate is a suitable sensor, the sensor becomes a bio-active sensor exhibiting the specificity of the bio-active material.

What is claimed is:

1. A sensor fabrication method comprising the steps of:
    a) polymerizing a layer of polysiloxane onto a substrate such that it sufficiently adheres thereto,
    wherein the substrate is selected from a group consisting of electrodes, diodes, field effect transistors, insulated gate field effect transistors, and metal oxide semiconductor field effect transistor; and
    b) adsorbing heptapeptide ligand selector molecules onto the layer of polysiloxane,
    wherein the steps of polymerizing and adsorbing occur concurrently and absent from an electrical voltage or current applied to the substrate and comprise: immersing the substrate in a solution or a suspension including polysiloxane-forming monomers and selector molecules, both polysiloxane-forming monomers and selector molecules being dispersed in the bulk of the solution or suspension, and
    wherein the polymerizing step and the adsorbing step hold heptapeptide ligand selector molecules onto the substrate by using hydrophobic silanol groups of the polysiloxane layer.

2. The sensor fabrication method according to claim 1 wherein the polymerizing step includes chemically bonding the polysiloxane layer to the substrate.

3. The sensor fabrication method according to claim 2 wherein the electrodes include a glass electrode.

4. The sensor fabrication method according to claim 3 wherein the glass electrode is an Indium-Tin-Oxide glass electrode.

5. The sensor fabrication method according to claim 3 wherein the glass electrode is a Metal-Oxide glass electrode.

6. The sensor fabrication method according to claim 1 further comprising:
    c) treating the substrate by exposing the substrate to NaOH.

7. The sensor fabrication method according to claim 1 further comprising:
    treating the substrate by exposing the substrate to NaOH.

8. The sensor fabrication method according to claim 7 wherein the trichlorosilane compound is one selected from a group consisting of: octenyltrichlorosilane, cyclohexlmethyltrichlorosilane, bromopropyltrichlorosilane, trichlorosilane, tert-butyltrichlorosilane, ethoxytrichlorosilane, methyltrichlorosilane, and pentyltrichlorosilane.

9. The sensor fabrication method according to claim 1 wherein the heptapeptide ligand selector molecules are specific to *Bacillus subtilis* spores, and wherein the sensor provides a distinct and observable potentiometric response to *Bacillus subtilis* spores.

10. The sensor fabrication method according to claim 1 wherein the heptapeptide ligand selector molecules are specific to *Bacillus anthracis* spores, and wherein the sensor provides a distinct and observable potentiometric response to *Bacillus anthracis* spores.

11. The sensor fabrication method of claim 1 wherein the step of adsorbing heptapeptide ligand selector molecules occurs in the presence of octadecyltrichlorosilane.

12. A sensor fabrication method comprising the steps of:
    a) polymerizing a layer of polysiloxane onto a substrate such that it sufficiently adheres thereto,
    wherein the substrate is selected from a group consisting of electrodes, diodes, field effect transistors, insulated gate field effect transistors, and metal oxide semiconductor field effect transistors; and
    b) adsorbing, onto the layer of polysiloxane, at least one of (A) selector molecules specific to *Bacillus subtilis* spores, wherein the sensor provides a distinct and observable potentiometric response to *Bacillus subtilis* spores, or (B) selector molecules specific to *Bacillus anthracis* spores, wherein the sensor provides a distinct and observable potentiometric response to *Bacillus anthracis* spores,
    wherein the steps of polymerizing and adsorbing occur concurrently and absent from an electrical voltage or current applied to the substrate and comprise: immersing the substrate in a solution or a suspension including polysiloxane-forming monomers and selector molecules, both polysiloxane-forming monomers and selector molecules being dispersed in the bulk of the solution or suspension, and
    wherein the polymerizing step and the adsorbing step hold heptapeptide ligand selector molecules onto the substrate by using hydrophobic silanol groups of the polysiloxane layer.

13. The sensor fabrication method according to claim 1, wherein the substrate is immersed in the solution or the suspension for a predetermined period that is optimized to produce a peak response to an analyte during a following testing.

14. The sensor fabrication method according to claim 13, wherein the predetermined period is approximately four minutes.

15. The sensor fabrication method according to claim 12, wherein the substrate is immersed in the solution or suspension for a predetermined period that is optimized to produce a peak response during a following testing.

16. The sensor fabrication method according to claim 15, wherein the predetermined period is approximately four minutes.

17. An anthrax sensor fabrication method comprising the steps of
    co-adsorbing polysiloxane-forming monomers and anthrax recognition elements from a solution or suspension, which have the monomers and recognition elements dispersed in its bulk, onto a substrate without the assistance of an electrical voltage or current applied to the substrate and
    immobilizing anthrax recognition elements among carbon chains of polysiloxane formed by polymerizing the polysiloxane-forming monomers.

* * * * *